(12) United States Patent
Weber et al.

(10) Patent No.: US 10,058,325 B2
(45) Date of Patent: Aug. 28, 2018

(54) SUTURE PASSER AND METHOD OF TISSUE REPAIR

(71) Applicant: Arthrex, Inc., Naples, FL (US)

(72) Inventors: Robert M. Weber, Chino Hills, CA (US); John P. Gauldoni, Naples, FL (US)

(73) Assignee: Arthrex, Inc., Naples, FL (US)

( * ) Notice: Subject to any disclaimer, the term of this patent is extended or adjusted under 35 U.S.C. 154(b) by 400 days.

(21) Appl. No.: 14/843,579

(22) Filed: Sep. 2, 2015

(65) Prior Publication Data

US 2016/0338691 A1 Nov. 24, 2016

Related U.S. Application Data

(60) Provisional application No. 62/163,777, filed on May 19, 2015.

(51) Int. Cl.
*A61B 17/04* (2006.01)
*A61B 17/06* (2006.01)

(52) U.S. Cl.
CPC ...... *A61B 17/0469* (2013.01); *A61B 17/0483* (2013.01); *A61B 17/0485* (2013.01); *A61B 2017/06042* (2013.01)

(58) Field of Classification Search
CPC ............ A61B 17/0469; A61B 17/0483; A61B 17/0485; A61B 2017/00349
See application file for complete search history.

(56) References Cited

U.S. PATENT DOCUMENTS

| | | | |
|---|---|---|---|
| 3,842,840 A * | 10/1974 | Schweizer | A61B 17/04 606/145 |
| 3,901,244 A * | 8/1975 | Schweizer | A61B 17/04 206/63.3 |
| 4,759,364 A * | 7/1988 | Boebel | A61B 17/0469 606/142 |
| 5,389,103 A * | 2/1995 | Melzer | A61B 17/0469 112/169 |
| 5,746,753 A | 5/1998 | Sullivan et al. | |
| 5,792,153 A * | 8/1998 | Swain | A61B 17/0469 112/169 |
| 6,551,330 B1 | 4/2003 | Bain et al. | |
| 6,770,084 B1 | 8/2004 | Bain et al. | |
| 6,893,448 B2 | 5/2005 | O'Quinn et al. | |
| 6,936,054 B2 | 8/2005 | Chu | |
| 7,083,628 B2 | 8/2006 | Bachman | |
| 7,377,926 B2 | 5/2008 | Topper et al. | |
| 7,544,199 B2 | 6/2009 | Bain et al. | |
| 7,815,654 B2 | 10/2010 | Chu | |
| 7,879,048 B2 | 2/2011 | Bain et al. | |
| 8,361,089 B2 | 1/2013 | Chu | |
| 8,469,974 B2 | 6/2013 | Skinlo et al. | |
| 8,764,771 B2 | 7/2014 | Chu | |
| 8,906,041 B2 | 12/2014 | Chu | |
| 9,271,719 B2 | 3/2016 | Skinlo et al. | |
| 2005/0251153 A1* | 11/2005 | Sakamoto | A61B 17/0469 606/139 |
| 2009/0069846 A1 | 3/2009 | Bull et al. | |
| 2010/0121352 A1 | 5/2010 | Murray et al. | |

(Continued)

*Primary Examiner* — Jonathan Miles
*Assistant Examiner* — Wade Miles
(74) *Attorney, Agent, or Firm* — Rubin and Rudman LLP (57) ABSTRACT

Instruments and methods for passing suture in tissue repair and other surgical procedures are disclosed.

12 Claims, 6 Drawing Sheets

(56) References Cited

U.S. PATENT DOCUMENTS

2010/0256657 A1 10/2010 Domingo
2013/0041387 A1 2/2013 Skinlo et al.
2013/0231669 A1 9/2013 Sinnott et al.
2014/0171980 A1 6/2014 Skinlo et al.

* cited by examiner

SUTURE PASSER AND METHOD OF TISSUE REPAIR

CROSS-REFERENCE TO RELATED APPLICATIONS

This application claims the benefit of U.S. Provisional Application No. 62/163,777, filed May 19, 2015, the disclosure of which is incorporated by reference in its entirety herein.

BACKGROUND

The present disclosure relates to surgical instruments for suturing tissue and methods of tissue repair. In particular, the present disclosure relates to a suture passer used to clamp tissue and pass suture through the tissue.

SUMMARY

A suture passer and methods for surgical repairs are disclosed. A suture passer can clamp or secure tissue (e.g., a capsule) in place, pass a needle through the tissue, load a flexible strand into the needle, and/or retract the needle with flexible strand back through the clamped tissue. A suture passer can include a securing mechanism that can capture a flexible strand and lock it into place. In an embodiment, a securing mechanism may be a spring-loaded suture clip configured to securely hold a flexible strand (e.g., suture) and then load the flexible strand into a hook and notch of the needle when the needle passes through an opening in the distal jaw.

A method of clamping and suturing tissue is also disclosed. In an embodiment, tissue can be clamped and sutured with a suture passer instrument.

DETAILED DESCRIPTION

A suture passer and surgical techniques for endoscopic surgical repairs, for example, arthroscopic surgeries, are disclosed. A suture passer can clamp or secure a tissue in place, pass a needle through the tissue, load a suture into the needle, and retract the needle with suture back through the clamped tissue. In an embodiment, the tissue can be a capsule. For example, a capsule can be the capsule of the humerus, knee, hip joint, temporomandibular joint, atlanto-axial joint, etc. A capsule can also be an interface that forms between an implanted device and the body's own soft tissues. A suture passer can facilitate precise suture placement in tissue that is typically difficult to retain and suture, in particular the capsular ligament of the hip.

A suture passing instrument can include an elongated tubular member that has a channel housing a needle. A handle assembly can comprise a trigger mechanism and a handle, the trigger mechanism being pivotally connected to the handle. A trigger mechanism can articulate a proximal jaw (movable jaw or movable member) relative to the tip of an instrument. A suture can be placed in a slot of a spring-loaded clip at the tip (stationary jaw or distal jaw) of an instrument. By squeezing a trigger mechanism, a movable jaw can move towards a stationary jaw, thereby securing contact with tissue and clamping the tissue between the jaws. By actuating a handle, a needle can be advanced relative to a body of the instrument. A needle can be pushed forward to displace a spring-loaded clip and suture in a direction about perpendicular to the longitudinal axis of the instrument. In an embodiment, an instrument may capture a suture extending within a slot in a tip (e.g., stationary jaw) and when pulled back, the suture (i.e., captured by the needle) passes through the tissue.

In an illustrative embodiment, a suture passing instrument comprises a securing mechanism that moves from a first location to a second location when a needle passes through a passage and out of a distal opening. A securing mechanism can include a coil spring-loaded suture clip. A suture clip as disclosed herein can include a transversal slot or opening. In an embodiment, a first jaw comprises a distal opening for needle passage. A first jaw can be fixedly mounted to a distal end of a shaft and a second jaw is located at least partially within the shaft. In an embodiment a second jaw is movable in respect to a first jaw. A securing mechanism can secure a flexible strand (e.g., suture) in tissue. A suture passing instrument can also include a handle assembly. A handle assembly can move a needle from a first position to a second position, which can also mover a second jaw with respect to a first jaw. In an illustrative embodiment, a spring loaded suture clip holds a flexible strand (e.g., suture) and then loads the flexible strand onto a needle (e.g., onto a hook of a needle), thereby passing the flexible strand from a first jaw to a second jaw.

A combined tissue clamping and suture passing instrument is also disclosed. A combined tissue clamping and suture passing instrument allows simultaneous clamping, holding, or securing of tissue (e.g., meniscal or capsular ligament) while allowing a flexible strand (for example, suture, suture wire, or a similar strand) to pass through the tissue that is clamped, held, or secured.

In an embodiment, a suture passer instrument comprises: a shaft having a longitudinal axis, a distal end, and a proximal end; a tip at the distal end of the shaft, the tip having an opening for a needle to pass through and a securing mechanism to allow secure placement of suture; and a needle with a capturing mechanism for capturing and retaining suture, wherein contact of the needle with the suture allows the suture to move in a direction about perpendicular to a longitudinal axis of the needle and of the shaft. A movable jaw (movable member, proximal member, or tissue clamp) may be disposed within the shaft and configured to slidably extend towards the tip.

Another exemplary suture passer instrument comprises: a shaft having a longitudinal axis, a distal end, and a proximal end; a stationary jaw (stationary member or tip) at the distal end of the shaft, the stationary jaw having an opening for a needle to pass through and a spring-loaded suture clip for securely holding a suture and then loading the suture into a hook of the needle when the needle passes through the opening; a movable jaw (movable member) disposed within the shaft and configured to slidably extend towards the stationary jaw; a needle with a hook for retaining suture; and an actuator configured to move the movable jaw with respect to the stationary jaw. An actuator can be within the shaft and at the distal end of the shaft.

Another embodiment of a suture passer instrument includes: a hollow shaft having a longitudinal axis, a distal end, and a proximal end; a mounted distal jaw fixedly mounted to the shaft at the distal end of the shaft; a proximal jaw (movable jaw, movable member, or tissue clamp) disposed at least partially within the shaft, the proximal jaw configured to slidably extend towards the mounted distal jaw to clamp tissue between the mounted distal jaw and the proximal jaw, and to retract from the distal jaw to release tissue clamped between the mounted distal jaw and the proximal jaw; a needle contained within the proximal jaw, the needle configured to slidably extend through tissue being clamped between the proximal jaw and the mounted distal jaw, where the needle can extend independently of the proximal jaw, the needle having a pointed end for piercing through tissue, and a hook configured to retain suture while the needle is pulled back through the tissue; the mounted distal jaw having an opening for the needle to pass through, and a spring-loaded suture clip configured to securely hold suture and then load the suture into the hook of the needle when the needle passes through the opening; and at least one of the surfaces of the proximal jaw and mounted distal jaw that come in contact with the tissue being textured or patterned to enhance the clamping, holding, or securing of the tissue (i.e., provided with a plurality of teeth or protuberances); and a handle configured to move the proximal jaw with respect to the mounted distal jaw.

Methods of suturing tissue are also disclosed. In an embodiment, tissue can be sutured with an instrument by securing a flexible strand within a spring-loaded clip of a tip of a suture passing instrument; capturing a flexible strand with a needle; and passing the flexible strand through tissue, wherein contact of the needle with the flexible strand causes movement of the flexible strand in a direction about perpendicular to a longitudinal axis of the needle.

Methods of clamping and suturing tissue are also disclosed. In an embodiment, tissue can be clamped and sutured with a single combined tissue clamping and suture passer instrument, for example a combined tissue clamping and suture passer instrument as disclosed herein. In an embodiment, a portion of tissue can be clamped and sutured with a single combined tissue clamping and suture passer instrument. In an illustrative embodiment, capsular hip ligament can be clamped and sutured with a single combined tissue clamping and suture passer instrument.

An exemplary method of clamping and suturing tissue comprises: (i) clamping, securing, or holding at least a portion of a tissue with a combined clamping-suture passing instrument; (ii) securing a flexible strand within a spring-loaded clip at a tip of the instrument; (iii) capturing the flexible strand with a needle; and (iv) pulling back the needle to pass the flexible strand through the clamped tissue.

In an illustrative embodiment, a method of clamping and suturing tissue includes clamping, securing, or holding at least a portion of a capsular hip ligament. In an illustrative embodiment, at least a portion of capsular ligament can be clamped and secured by a combined suture passer and tissue clamping instrument. In an embodiment, a method of clamping and suturing capsular ligament includes securing a flexible strand into a spring-loaded clip of a tip of the combined instrument. In an illustrative embodiment, a method of clamping and suturing capsular ligament includes advancing a tissue clamp towards the tip of the combined instrument to clamp and secure the capsular ligament between the tissue clamp and the tip, and advancing a needle towards the tip to capture the flexible strand from the spring-loaded clip and pass the flexible strand through the capsular ligament.

Referring now to the drawings, where like elements are designated by like reference numerals, FIGS. 1-6 illustrate various structural elements of instrument 100 (suture passer 100, suture passing instrument 100, or combined tissue clamping and suture passing instrument 100) provided with needle 55 designed to engage and pass a flexible strand 80 (e.g., suture) in a linear direction about parallel to the longitudinal axis of the instrument. FIGS. 7-15 illustrate an exemplary method of capsular repair with instrument 100.

Instrument 100 comprises an elongated tubular member or shaft 12 having a longitudinal axis 12*a*, a proximal end 11, a distal end 13 and an axial throughbore therein (not shown). Elongated tubular member 12 may be a tube or a narrow-diameter rod of dimensions that permit the tubular member to be introduced through an associated cannula (for example, an 8.25 cannula) in a minimally invasive procedure, such as arthroscopic or other endoscopic procedures, or into a body cavity, such as the abdominal cavity.

Elongated tubular member 12 connects a handle assembly 20 with a pair of jaws 10, 40. Distal jaw 10 (first jaw 10, tip 10, or stationary jaw 10) is provided at the distal end 13 of the instrument and is preferably integral with (fixedly mounted to) the tubular member 12. Proximal jaw 40 (Second jaw 40, movable member 40, or tissue clamp 40) is movable with respect to the distal jaw 10 and is slidingly received in the axial throughbore (channel) of the elongated tubular member 12.

Distal jaw 10 of instrument 100 includes a securing mechanism 30 provided at the distal end of the jaw 10 that is configured to releasably support a length of flexible strand 80 therein. The securing mechanism 30 is formed integrally with the jaw 10 and includes a clip 31 with opening 33, a spring 35, and a stop pin 37. Clip 31 may be a spring-loaded suture clip supported by coil spring 35. Opening 33 may be a transversal suture loading slot 33. Slot 33 can be arcuate, to allow suture or a strand of flexible material to extend therethrough, in a position about perpendicular to the longitudinal axis of the elongated tubular member. Slot 33 is formed to dimensions smaller than those of the suture slots known in the art, to prevent unwanted sutures and tissue from inadvertently getting hooked. Slot 33 may include a transversal channel with two lateral slots, grooves or wedges, each of the lateral slots, grooves or wedges being disposed on each end of the transversal slot, to allow increased suture positioning for future suture manipulation with the needle construct.

In an embodiment, the securing mechanism 30 is designed to allow secure placement of the flexible strand within it, while allowing a needle to travel in a to- and fro-direction relative to the transversal flexible strand. In this manner, when needle 55 is advanced to travel toward the distal jaw 10, to capture the flexible strand 80, the needle can pass past the transversal slot to allow capturing of the flexible strand in notch 56 of hook 55*a*, and then pull back in an opposite direction (again passing past the transversal slot) to allow pulling of the flexible strand away from the distal end of the instrument.

When disposed in the slot 33, flexible strand 80 is placed about transversal to the longitudinal axis 12*a*, with the ends of the flexible being pulled in a transversal direction relative to the slot such that the flexible is wedged securely into the slot 33. When needle 55 is in the non-working (retracted or non-deployed position), at a first location $L_1$ (FIG. 9), flexible strand 80 is about coplanar with longitudinal axis 12a of the instrument (which coincides with longitudinal axis 50a of the needle and longitudinal axis 40a of movable member 40). Contact of needle 55 with flexible strand 80 causes the flexible strand 80 and clip 31 to move a distance "d" relative to the longitudinal axis 12a of the instrument to a second location $L_2$ (FIG. 11), wherein the flexible strand 80 is non-planar with the longitudinal axis 12a (which coincides with longitudinal axis 50a of the needle and longitudinal axis 40a of movable member 40). The flexible strand can be a braided suture, for example FiberWire® (Artbrex, Inc., Naples, Fla.).

Figure 2:
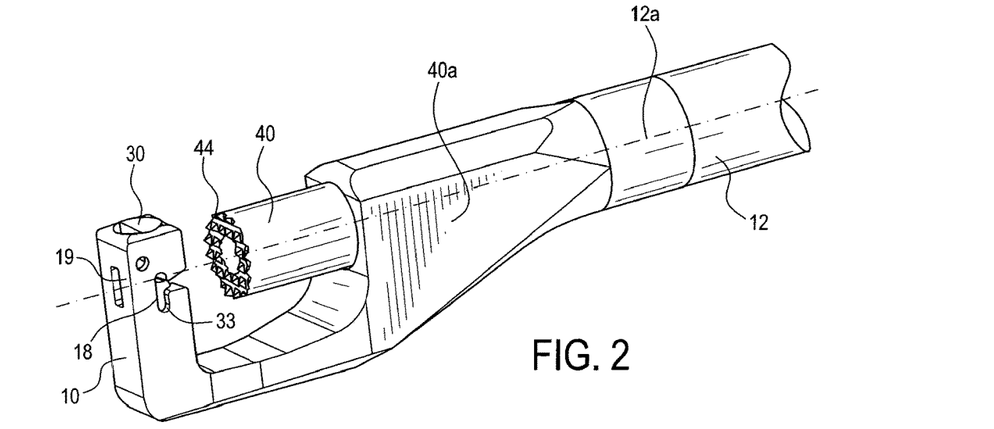
FIG. 2 is an enlarged perspective view of the distal end of the suture passing instrument of FIG. 1.
Figure 3:
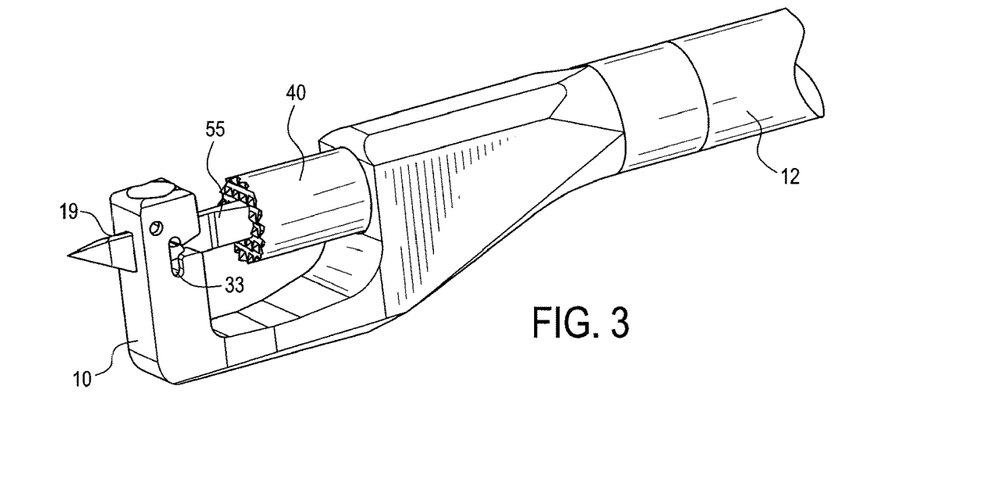
FIG. 3 is another enlarged perspective view of the distal end of the suture passing instrument of FIG. 1.
Figure 4:
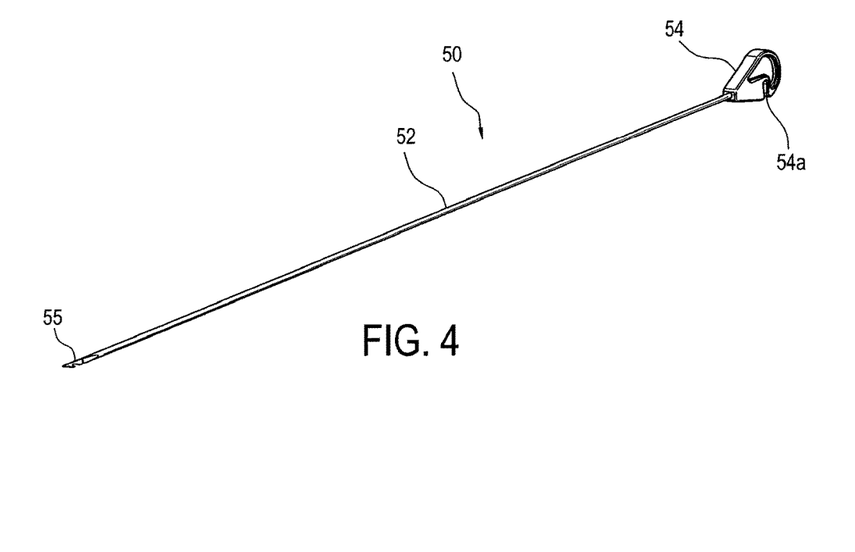
FIG. 4 is a perspective view of the needle of the suture passing instrument of FIG. 1.

Distal jaw 10 is also provided with a needle passage 18 and an opening 19 that allows needle 55 to pass and extend therethrough, as illustrated in FIGS. 2 and 3, for example. Opening 19 is provided in a most distal end of jaw 10 and communicates with the needle passage 18. Preferably, the opening 19 has the shape of a channel with a rectangular or square cross-section to allow the needle (which may have a generally square or rectangular cross-section, or a generally circular cross-section) to pass therethrough.

As shown in FIGS. 2 and 3, distal opening 19 allows needle 55 to exit in a direction about parallel to the longitudinal axis of the instrument. In an exemplary embodiment, needle 55 is housed in proximal jaw 40 (movable jaw 40) which is slidingly received in the axial throughbore (channel) of the elongated tubular member 12. Needle 55 is substantially disposed within the proximal jaw 40 of the shaft 12 when the needle is in a non-operative, non-piercing, or non-deployed position. In an operative position, the needle is advanced distally to exit openings 19 in the distal jaw 10. Needle 55 may be also provided independently from movable member 40, i.e., slidingly received in a throughbore (channel) of the elongated tubular member 12.

Figure 5:
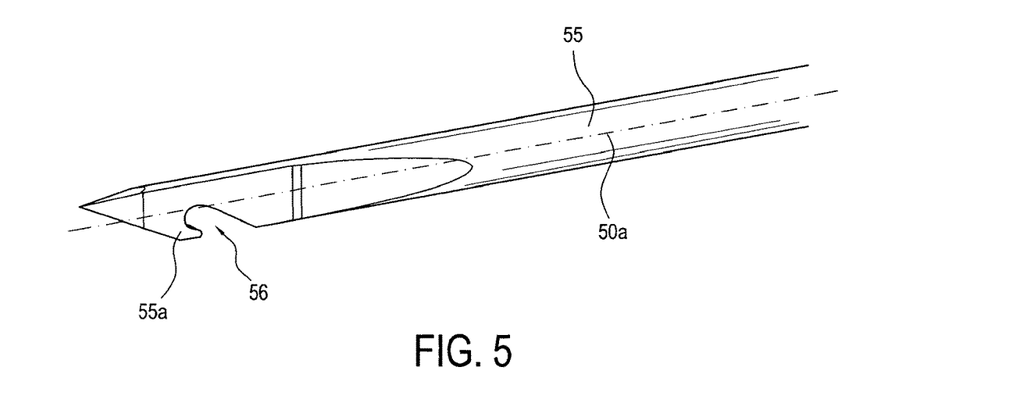
FIG. 5 is an enlarged view of the distal end of the needle of FIG. 4.

Preferably, needle 55 has a narrow, pointed tip at a distal end and a hook 55a that is adjacent the pointed tip and that has an opening (notch) 56 facing the proximal end of the instrument (FIG. 5). The opening 56 of hook 55a also preferably faces downwardly (i.e., in a plane extending below the longitudinal axis 12a of the instrument). Needle 55 may preferably be formed of nitinol or other suitable material.

Figure 1:
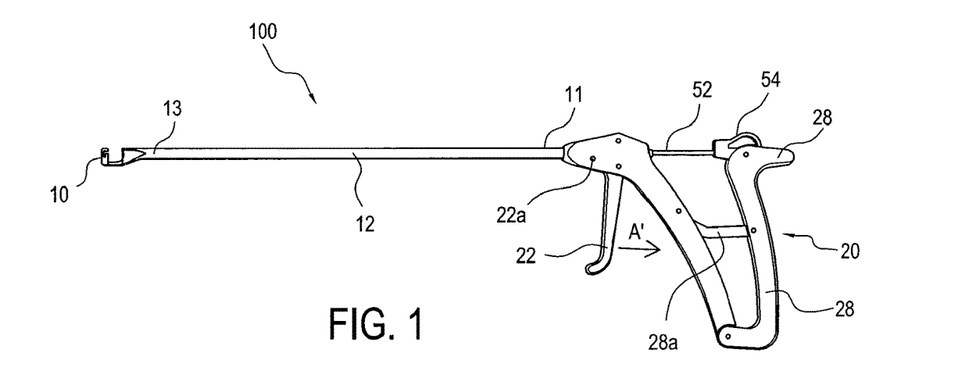
FIG. 1 is a perspective view of the suture passing instrument according to an exemplary embodiment.

Needle actuator 50 (FIG. 4) houses needle 55 and comprises shaft 52 (which is slidingly received in the axial throughbore (channel) of the movable member 40 or elongated tubular member 12) and a most proximal end 54 provided with a slot that is engaged securely into a cross pin 54a on the proximal end of handle 28 of the suture passing instrument (FIG. 1). The needle actuator facilitates passing the flexible strand 80 through the tissue. In use, needle actuator 50 is actuated relative to the longitudinal axis 12a of the tubular member, and needle 55 is pushed forward toward opening 19 to exit the opening as shown in FIGS. 2 and 11-13, for example.

Handle assembly 20 of the suturing instrument 100 (illustrated in FIG. 1) is provided at the proximal end 11 of the instrument and includes a trigger mechanism 22 (or actuating mechanism 22) and a handle 28, the trigger mechanism 22 being pivotally connected to the handle 28. The trigger mechanism 22 may consist of a finger lever 22 which, when actuated, is designed to move the proximal jaw 40 (movable member 40) relative to the distal jaw 10 (tip 10). The finger lever 22 is designed to move from a first position to a second position, with a spring 22a provided to maintain tension on the finger lever 22 and to force the finger lever 22 to go back to a default position. At its default position, the finger lever 22 is farthest from the distal end of the handle 28.

Instrument 100 further includes an actuator (not shown), which is provided within the shaft 12 and at the distal end of the shaft. The actuator is connected to the finger lever 22 and is designed to move the movable jaw 40 from a first position to a second position as the finger lever 22 is moved from a first position to a second position, and to clamp or secure tissue 90 between the movable jaw 40 and the tip or stationary jaw 10.

The proximal and distal ends of the handle 28 are connected via a link 28a and tension between the proximal and distal ends may be additionally maintained using springs 28b (not shown). By actuating the hand mechanism 20 (i.e., by bringing together the proximal and distal ends of the handle 28), pusher 54 of the needle actuator 50 advances needle 55 to capture the flexible strand 80 positioned within slot 33, and to further pull back the flexible strand 80 (captured in notch 56 of hook 55a of the needle) through tissue to be sutured.

Figure 6:
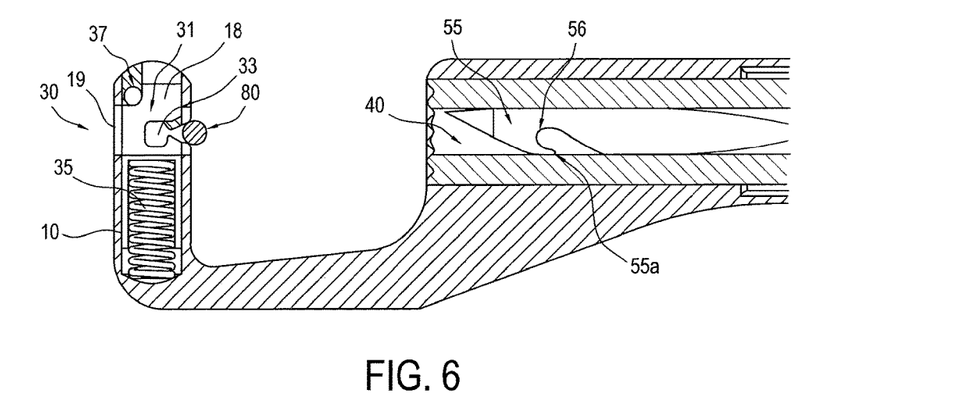
FIG. 6 is an enlarged cross-sectional view of the distal end of the suture passing instrument of FIG. 1, with the tissue clamp and needle in the retracted position.

FIG. 6 illustrates the positioning of the suture clip 31 relative to the coil spring 35 within stationary jaw or tip 10. When the flexible strand 80 is loaded onto the transversal slot 33, the transversal slot 33 and flexible strand 80 are about coplanar with longitudinal axis 12a of the instrument (which in turn coincides with longitudinal axis 50a of needle 55, and longitudinal axis 40a of movable member 40).

FIGS. 7-15 illustrate an exemplary method of tissue repair (e.g., capsular repair) with instrument 100 and exemplary suture 80.

Figure 7:
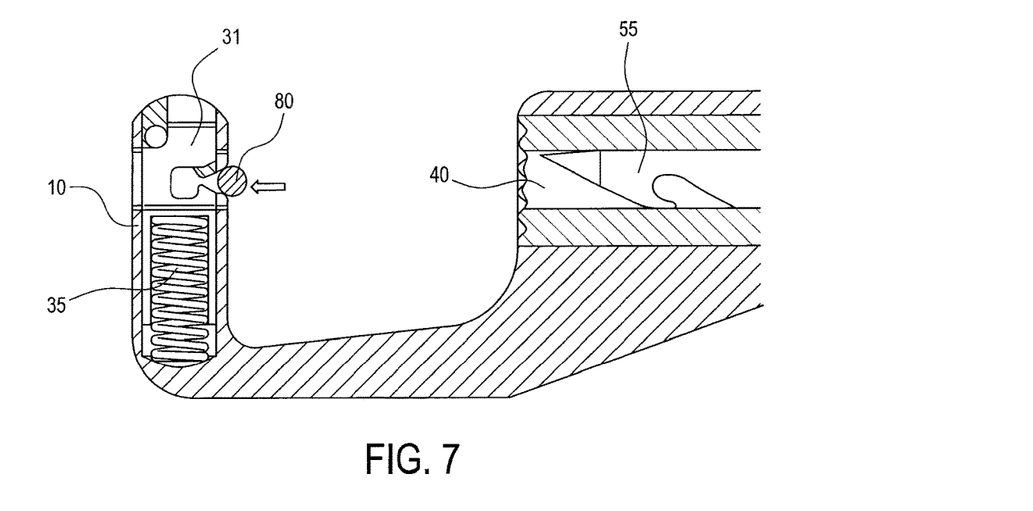
FIGS. 7-15 illustrate an exemplary method of tissue repair with the suture passing instrument of FIG. 1.

FIG. 7: suture loop 80 is pulled into slot 33 of spring loaded clip 31.

Figure 8:
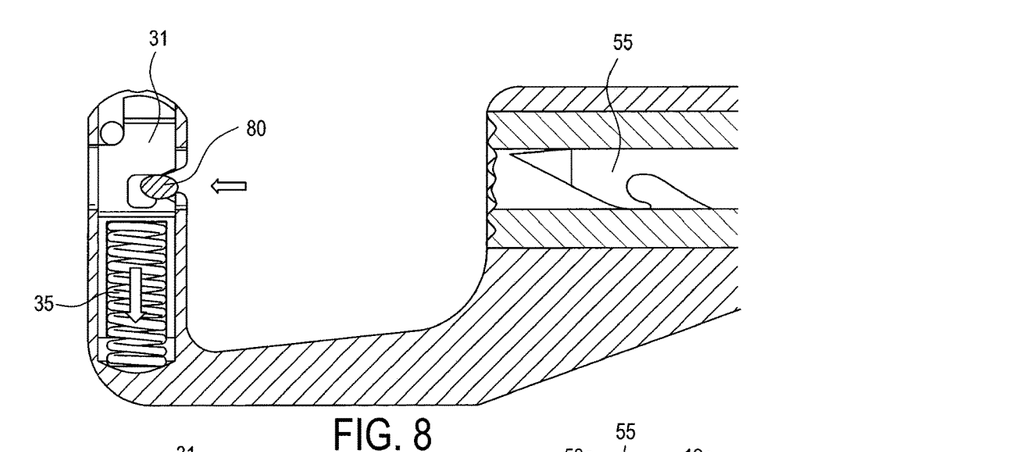

FIG. 8: spring loaded clip 31 moves down as suture 80 enters slot 33.

Figure 9:
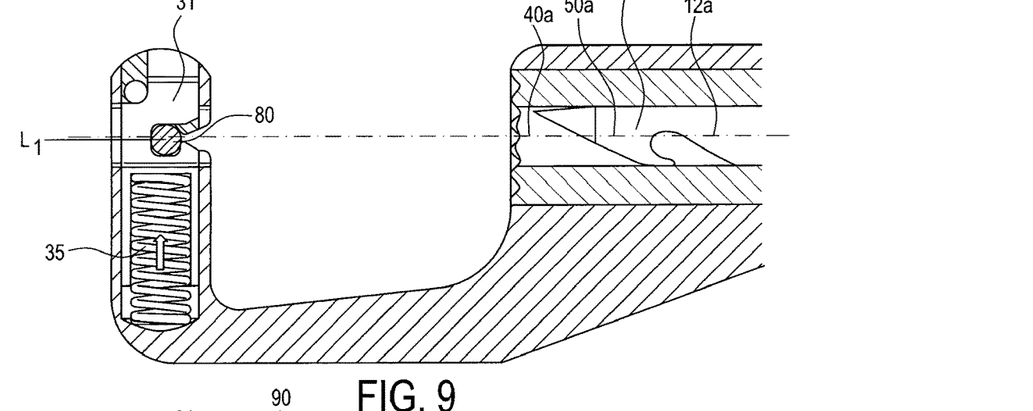

FIG. 9: when suture 80 is in slot 33, the clip 31 springs back up holding suture 80 in place.

Figure 10:
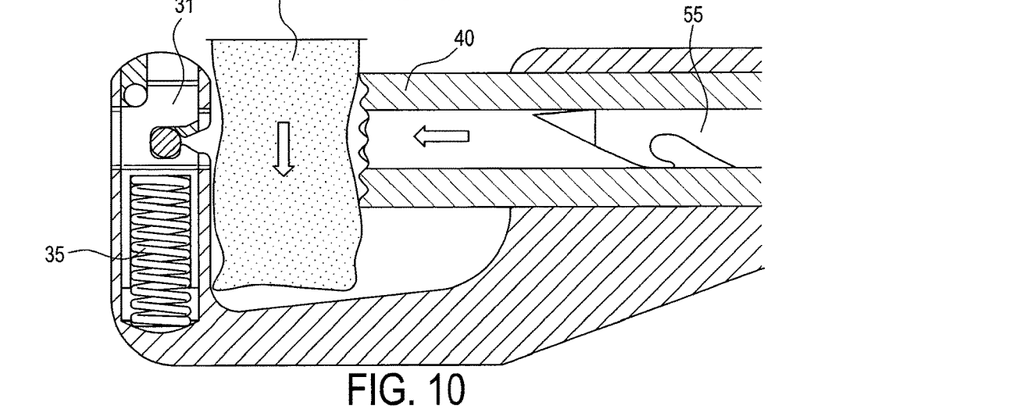

FIG. 10: tissue 90 is inserted and tissue clamp 40 (proximal jaw or movable member 40) is advanced to hold tissue 90 securely; tissue 90 is clamped or secured between the pair of jaws 10, 40 (i.e., tip 10 and tissue clamp 40).

Figure 11:
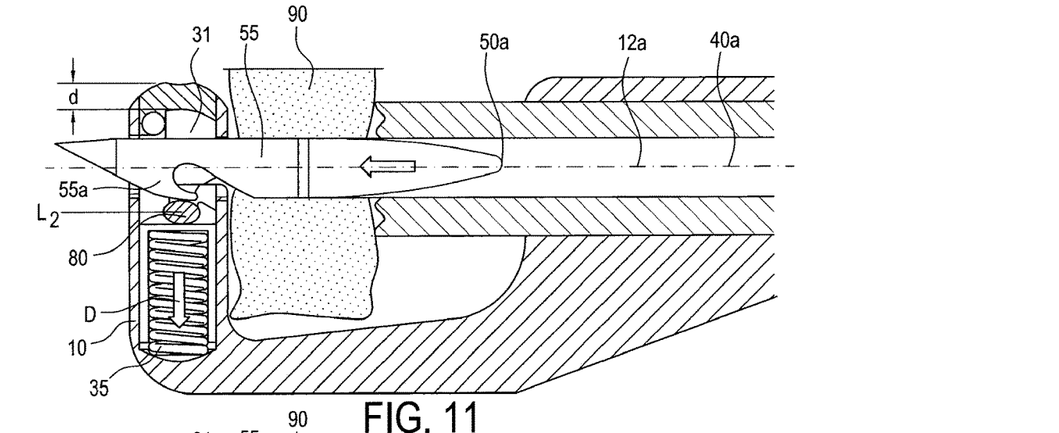

FIG. 11: needle 55 is advanced to penetrate tissue 90, pushing suture 80 and clip 31 down; needle 55 is advanced in the direction of arrow A; suture and clip are pushed down a distance "d" of about 2-5 mm in the direction of arrow D (i.e., in a direction about perpendicular to the direction of arrow A).

Figure 12:
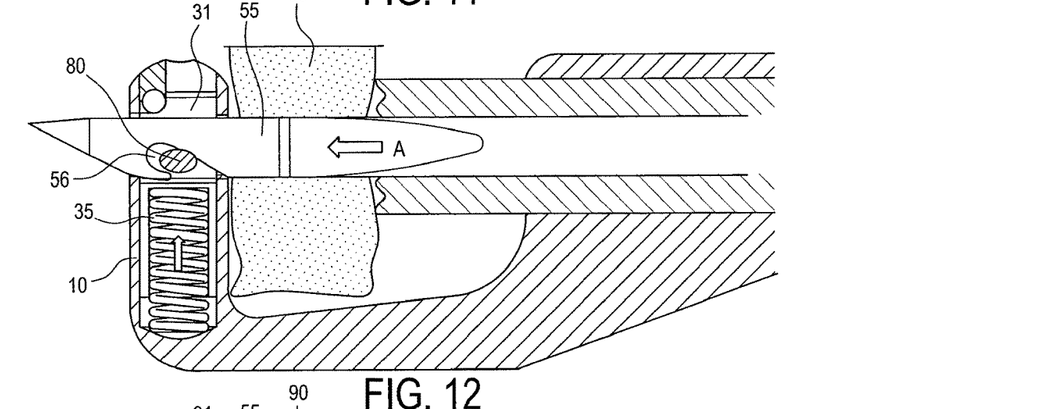

FIG. 12: when the needle hook 55a passes the suture 80, the clip 31 rises, pushing suture 80 into the needle notch 56; the clip rises or returns to the original position.

Figure 13:
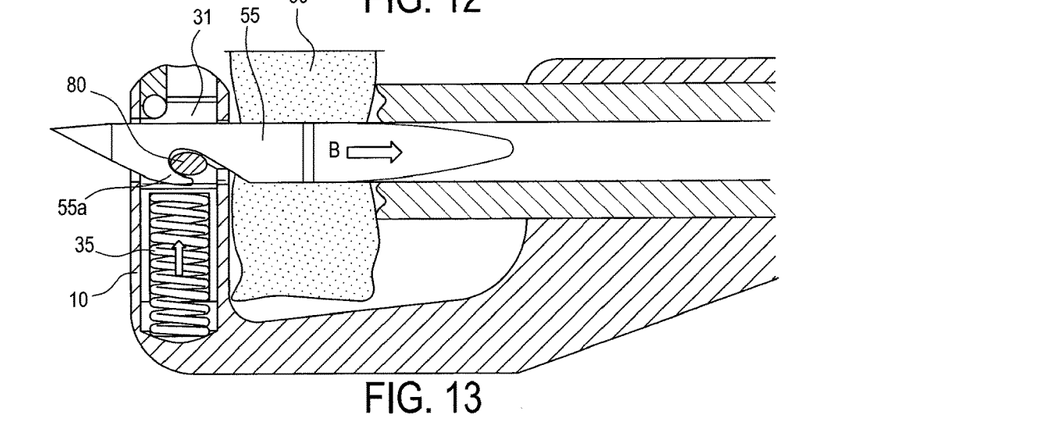

FIG. 13: the needle 55 is pulled back, retrieving suture 80 from tip 10 and clip 31; needle 55 is pulled back in the direction of arrow B.

Figure 14:
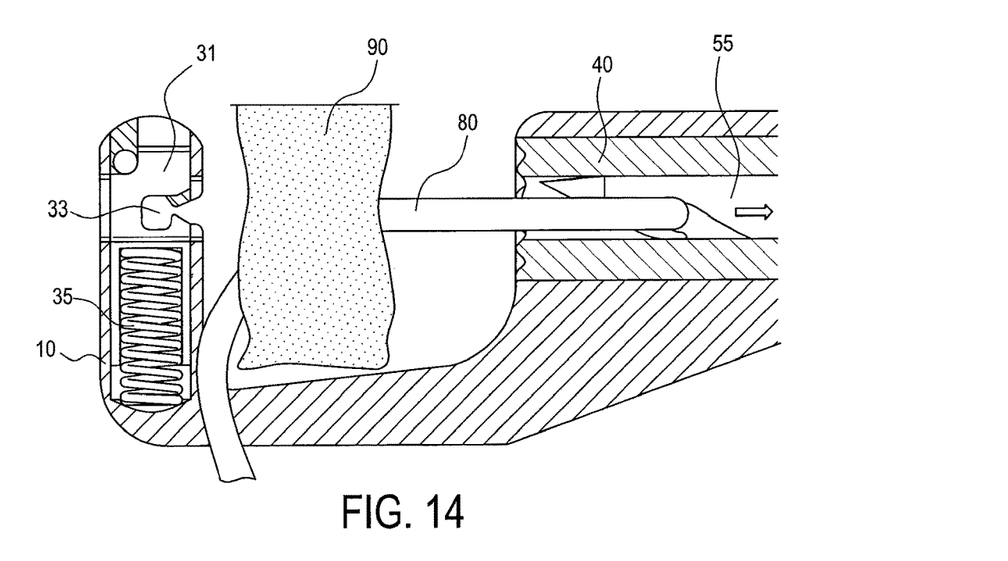

FIG. 14: the needle 55 pulls suture 80 back through the tissue 90.

Figure 15:
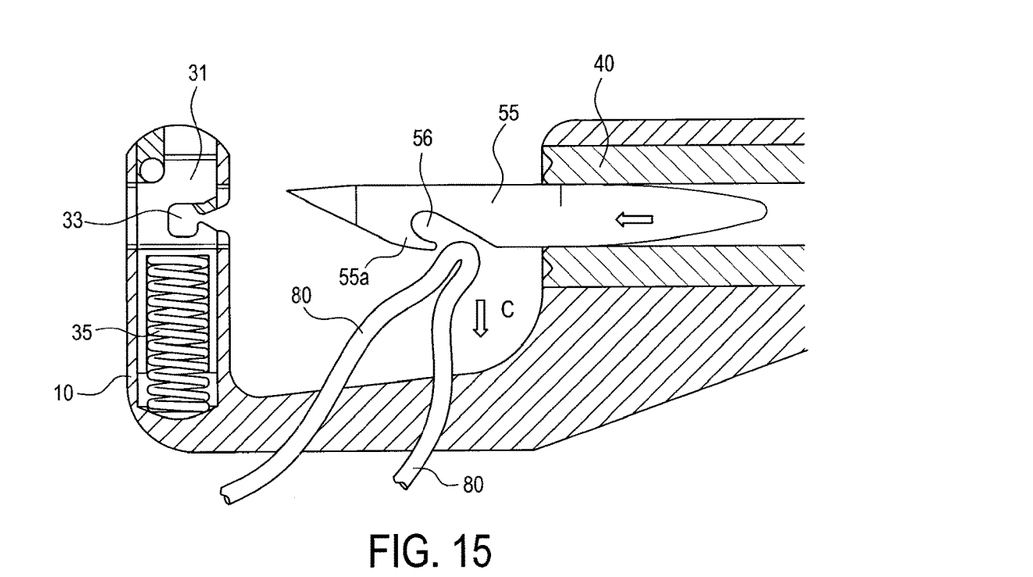

FIG. 15: advance the needle 55 and pull down on suture 80 to release; suture 80 is pulled down in the direction of arrow C.

In use, and as detailed above, a suture 80 can be loaded into spring-loaded suture clip 31 located in mounted distal jaw 10 of the instrument 100. With a suture securely retained in spring-loaded suture clip 31, instrument 100 can be positioned so as to retain target tissue 90 in the tip of the instrument 100. Proximal jaw 40, located within a hollow shaft 12 of instrument 100, is advanced forward to clamp tissue 90 securely between proximal jaw 40 and distal jaw 10. Once tissue 90 is secured, needle 55 contained within proximal jaw 40 is advanced forward through tissue 90. Needle 55 has a pointed tip for piercing tissue, and a hook 55a and notch 56 configured to retain suture 80. Needle 55 may be advanced through tissue 90 and through opening 19 in distal jaw 10. When needle 55 passes through opening 19 in distal jaw 10, needle 55 pushes down spring-loaded suture clip 31 for a distance "d," allowing needle 55 to continue passing through opening 19 without puncturing suture 80. When hook 55a of the needle 55 reaches spring-loaded clip 31, suture 80 can be loaded into a needle hook and notch 56 by action of spring 35. Needle 55, now with suture 80 loaded, can be pulled back through the clamped tissue 90. After needle 55 is completely pulled back through tissue 90, proximal jaw 40 may be pulled back, releasing the now-sutured tissue 90.

A method of employing instrument 100 begins by loading the needle 55 into the cannulation on the proximal end of the shaft 12 of instrument 100. The slot on the proximal end 54 of the needle actuator 50 is engaged securely into cross pin 54a on the proximal end of handle 28 of the instrument.

Suture 80 is loaded into the transversal slot 33 on the distal jaw 10 of the instrument 100. Using the finger lever 22 on the suture passing instrument 100 (i.e., actuating the finger lever 22 in the direction of arrow A' of FIG. 1), the proximal jaw 40 extends towards the distal jaw 10 and tissue 90 is clamped between the two jaws.

With the tissue 90 clamped between the jaws, needle 55 is advanced distally such that the needle exits the opening 19 on the distal jaw 10. The pointed tip of the needle 55 pierces completely through the tissue (e.g., articular capsule or tendon) and then the hook 55a on the needle 55 pushes the suture 80 (loaded in the slot 33 of the distal jaw 10) together with the clip 31 a distance "d" in the direction of arrow D (FIG. 11). By releasing the distal and proximal ends of handle 28, the needle 55 is pulled back and the suture 80 is captured in hook 55a and notch 56 of the needle, and pulled back through the soft tissue 90 in a direction about parallel to longitudinal axis 12a of the shaft 12 of the instrument. By releasing the finger lever 22, the proximal jaw 40 is retracted (pulls away from the distal jaw 10) and the tissue 90 is released.

A suture passer as disclosed herein may be employed in various surgical medical procedures for advancing a suture in proximity of a surgical site. A suture passer as disclosed herein may also be employed with a suture and a cannulated instrument during such surgical procedures. For example, instrument 100 may be employed in endoscopic surgery. The term "endoscopic surgery" refers to surgical procedures within a patient's body through small openings as opposed to conventional open surgery through large incisions. Additionally, a suture passer as disclosed herein may be utilized in other general surgical and specialty procedures that require suturing. A suture passer as disclosed herein may be also used in repairs where suture visibility or finger access can be limited.

It will be appreciated, of course, that while a suture passer as disclosed herein may be particularly useful for performing remote procedures through access sheaths, trocars and cannulated surgical instruments, a suture passer as disclosed herein can also be used in open surgical procedures.

In an illustrative embodiment, a method of suturing tissue using a suture passer comprises: (i) engaging a flexible strand within a slot 33 of a securing mechanism 30 at the tip 10 of the instrument; (ii) advancing a needle 55 through a passage in tip 10 of the instrument, and displacing the flexible strand 80 and the securing mechanism 30 in a direction about perpendicular to a longitudinal axis 12a of the instrument; and (iii) subsequently, capturing the flexible strand 80 with the needle 55 and advancing the flexible strand 80 in a direction about parallel to the longitudinal axis 12a of the instrument and through tissue 90.

According to another exemplary and illustrative embodiment only, a method of suturing a tissue using the suture passing instrument 100 comprises: (i) loading a needle 55 onto the instrument; (ii) loading a suture 80 into a slot 33 of a spring-loaded clip 31 provided at the tip of a distal jaw 10 of the instrument; (iii) bringing a proximal jaw 40 towards the distal jaw 10 by actuating a finger lever 22, so that the proximal jaw 40 and the distal jaw 10 clamp tissue 90 therebetween; (iv) actuating a handle 28 to advance the needle 55 into a first direction (towards the suture loaded onto the slot of the distal jaw), passing the suture 80 and pushing the suture 80 and the spring-loaded clip 31 in a direction about perpendicular to the longitudinal axis 50a of the needle 55; (v) pulling the needle 55 in a second direction which is opposite the first direction, and capturing the suture 80 with a hook 56 and notch 56a of the needle 55; and (vi) pulling the suture 80 through the tissue 90 in a direction about parallel to the longitudinal axis 12a of the instrument.

A suture passing instrument 100 comprises: a shaft 12 having a longitudinal axis 12a, a distal end 13, and a proximal end 11; a first jaw 10 fixedly mounted to the distal end of the shaft 12, the first jaw 10 having a passage 18 for receiving a needle 55, and a distal opening 19 to allow the needle 55 to pass therethrough; a second jaw 40 located at least partially within the shaft, the second jaw 40 being movable with respect to the first jaw 10; and a handle assembly 20 configured to move the needle 55 from a first position to a second position, and to move the second jaw 40 with respect to the first jaw 10, wherein the first jaw 10 comprises a securing mechanism 30 to secure a flexible strand 80 at its most distal end, the securing mechanism 30 being configured to move from a first location to a second location when the needle 55 passes through the passage 18 and out of the distal opening 19 of the first jaw 10.

A flexible strand may be a suture strand or any suture-like material known in the art that could pass through tissue. A flexible strand may include a high-strength suture, such as an ultrahigh molecular weight polyethylene (UHMWPE) suture. High strength suture may be a FiberWire® suture (Arthrex). FiberWire® suture is formed of an advanced, high-strength fiber material, namely ultrahigh molecular weight polyethylene (UHMWPE), sold under the tradenames Spectra® (Honeywell International Inc., Colonial Heights, Va.) and Dyneema® (DSM N.V., Heerlen, the Netherlands), braided with at least one other fiber, natural or synthetic, to form lengths of suture material.

What is claimed is:

1. A suture passing instrument comprising:
   a shaft having a longitudinal axis, a distal end, and a proximal end;
   a first jaw and a second jaw, and a needle mounted on the second jaw;
   the first jaw fixedly mounted to the distal end of the shaft, the first jaw having a passage for receiving the needle, and a distal opening to allow the needle to pass therethrough;
   the second jaw located at least partially within the shaft, the second jaw being movable with respect to the first jaw; and
   a handle assembly configured to move the needle from a first position to a second position, and to move the second jaw with respect to the first jaw, wherein the first jaw comprises a securing mechanism to secure a flexible strand, wherein the securing mechanism includes a spring-loaded suture clip;

wherein the securing mechanism is configured to move from a first location to a second location when the needle moves from the first position to the second position passing through the passage and out of the distal opening of the first jaw, and wherein at the first location, a portion of the flexible strand contacting the securing mechanism is about coplanar with the longitudinal axis of the shaft, and wherein, at the second location, the portion of the flexible strand contacting the securing mechanism is non-planar with the longitudinal axis of the shaft.

2. The suture passing instrument of claim 1 wherein the spring-loaded suture clip comprises a transversal slot or opening, a coil spring, and a stop pin.

3. The suture passing instrument of claim 1, wherein the spring-loaded suture clip moves a distance of about 2-5 mm between the first location and the second location.

4. The suture passing instrument of claim 3, wherein the spring-loaded clip moves in a direction about perpendicular to the longitudinal axis of the shaft.

5. The suture passing instrument of claim 1, wherein the flexible strand is pulled by the needle in a direction about parallel to the longitudinal axis of the shaft.

6. The suture passing instrument of claim 1, wherein the handle assembly comprises a handle and a trigger mechanism, wherein the handle comprises a proximal member and a distal member, and wherein the trigger mechanism comprises a finger lever being pivotally connected to the distal member of the handle.

7. The suture passing instrument of claim 1, wherein the needle is provided with a sharp tip, a hook, and a notch.

8. The suture passing instrument of claim 1, wherein the second jaw is a movable member provided with a plurality of teeth.

9. The suture passing instrument of claim 1, wherein the tissue is capsular ligament or meniscus.

10. The suture passing instrument of claim 1, wherein the tissue is soft tissue.

11. The suture passing instrument of claim 1, wherein the flexible strand is a braided suture comprising a plurality of high strength fibers.

12. A method of suturing tissue with a suture passing instrument as recited in claim 1 comprising:

moving a spring-loaded suture clip with a flexible strand from a first location to a second location, wherein the flexible strand is about coplanar with a longitudinal axis of the instrument in the first location, and is non-planar with the longitudinal axis of the instrument in the second location;

capturing the flexible strand with a needle; and advancing the needle in a second direction which is opposite the first direction.

\* \* \* \* \*